United States Patent [19]

Romrell

[11] 4,033,179
[45] July 5, 1977

[54] ACOUSTIC EMISSION MONITORING SYSTEM

[75] Inventor: Delwin M. Romrell, Richland, Wash.

[73] Assignee: Westinghouse Electric Corporation, Pittsburgh, Pa.

[22] Filed: Mar. 7, 1975

[21] Appl. No.: 556,354

[52] U.S. Cl. .................................. 73/71.4; 340/15
[51] Int. Cl.² ......................................... G01N 9/18
[58] Field of Search ............ 340/15; 73/67 R, 67.3, 73/69, 88 R, 88.3, 71.4

[56] References Cited
UNITED STATES PATENTS

| | | | |
|---|---|---|---|
| 3,545,262 | 12/1970 | Steele et al. | 73/88.3 |
| 3,713,127 | 1/1973 | Keledy et al. | 73/88.3 |

OTHER PUBLICATIONS

Schofield, *Utilization of Acoustic Emission for In-Service Inspection*, Instn. Mech. Engrs.
Nakamura, *Acoustic Emission Monitoring System for Detection of Cracks in a Complex Structure*, presented 3-9-70 at Conference of the Amer. Soc. for Nondestruct. Test.

*Primary Examiner*—T.H. Tubbesing
*Assistant Examiner*—T. M. Blum
*Attorney, Agent, or Firm*—Z. L. Dermer; D. C. Abeles

[57] ABSTRACT

Methods and apparatus for identifying the source location of acoustic emissions generated within an acoustically conductive medium. A plurality of acoustic receivers are communicably coupled to the surface of the medium at a corresponding number of spaced locations. The differences in the reception time of the respective sensors in response to a given acoustic event are measured among various sensor combinations prescribed by the monitoring mode employed. Acoustic reception response encountered subsequent to the reception by a predetermined number of the prescribed sensor combinations are inhibited from being communicated to the processing circuitry, while the time measurements obtained from the prescribed sensor combinations are translated into a position measurement representative of the location on the surface most proximate the source of the emission. The apparatus is programmable to function in six separate and five distinct operating modes employing either two, three or four sensory locations. In its preferred arrangement the apparatus of this invention will re-initiate a monitoring interval if the predetermined number of sensors do not respond to a particular emission within a given time period.

19 Claims, 4 Drawing Figures

ACOUSTIC EMISSION MONITORING SYSTEM

BACKGROUND OF THE INVENTION

The invention described herein was made in the course of, or under a contract with the United States Atomic Energy Commission.

The invention generally pertains to methods and apparatus for monitoring acoustic emissions and more particularly to methods and apparatus that identify the source location of such emissions.

Non-destructive testing of metal formations, such as weld seams, have been employed for a number of years to detect discontinuities that might otherwise effect the reliability of operating components. If it were not for such inspection techniques, flaws could result in malfunctions during use, which are likely to cause substantial and sometimes irreparable damage. In recent years acoustic insepction techniques have been developed which have significantly advanced the state of the art. Usually such techniques employ ultrasonic technology in various embodiments that basically rely on externally generated acoustic pulses which are transmitted within the member being inspected. The time of travel of reflected signals are interpreted to identify the presence and location of flaws.

The application of ultrasonic non-destructive testing techniques to weldments usually requires elaborate scanning arrangements which are normally applicable only after the weld joints have cooled. Flaws noted will have to be corrected by substantially re-initiating the entire welding process. This type of procedure is not only time consuming, but expensive and often results in compromises in the acceptability of the structural integrity of the member in question.

While acoustic emission monitoring has been employed in non-destructive testing applications, such procedures have encountered great difficulties in identifying source locations of flaws in varying geometries of materials. In addition, such procedures have experienced erroneous results engendered by multiple acoustic emissions occurring within the same time frame.

Accordingly, a new system is desired that will facilitate on-line monitoring of welding processes to identify and locate the formation of flaws. Furthermore, such a system is desired that can segregate out multiple acoustic events and accommodate structures of varying geometrics.

SUMMARY OF THE INVENTION

Briefly, this invention provides methods and apparatus for identifying the source location of acoustic emissions generated within an acoustically conductive medium. The apparatus and various methods of this invention employ a plurality of acoustic receivers which are communicably coupled to the surface of the medium at a corresponding number of spaced locations. The differences in the reception time of the respective sensors in response to a given acoustic event are measured among various sensor combinations prescribed by the monitoring modes employed. Acoustic reception responses encountered subsequent to the reception by a predetermined number of the prescribed sensor combinations are inhibited from being communicated to the processing circuitry of the apparatus of this invention in order to isolate the particular acoustic emission of interest, while the time measurements obtained from the prescribed sensor combinations are translated into a position measurement representative of location on the surface most proximate the source of the emission. The apparatus of this invention is programmable to function in any one of five distinct operating modes, preferably employing either two, three or four sensory locations. In its preferred arrangement the apparatus will re-initiate a monitoring interval if a predetermined number of sensors do not respond to a particular emission within a given time period.

According to one programmed mode of operation taught by the method of this invention the apparatus will monitor the time difference in reception between a first and second sensor, blocking subsequent acoustic responses while the difference in time is translated into a position measurement.

In a second mode of operation according to the method of this invention the apparatus will monitor the difference in acoustic reception time between the sensors in two separate sensor pairs, inhibiting further acoustic responses until the two time measurements are coordinated to provide a positional measurement indicative of the location of the source of the acoustic emission.

In a third mode of operation the apparatus will monitor the time difference in acoustic reception between the first two of three sensors responding to an acoustic event, blocking responses until the time difference is translated into a positional measurement identifying the location of the acoustic source.

In a fourth mode of operation the apparatus will monitor the time difference in reception respectively between first and second, second and third and third and fourth sensor locations inhibiting further acoustic responses until the location of the acoustic source has been identified.

In a fifth mode of operation the apparatus of this invention will monitor acoustic receptions of two separate sensor pairs and measure the time difference between the sensor of the first pair first exhibiting an acoustic response, inhibiting further responses until the location of the acoustic source has been identified.

In this way the reliability of the positional readings are assured and various geometries are accommodated in a system that possesses an on-line monitoring capability.

BRIEF DESCRIPTION OF THE DRAWINGS

For a better understanding of the invention, reference may be had to the preferred embodiment, exemplary of the invention, shown in the accompanying drawings, in which.

DESCRIPTION OF THE PREFERRED EMBODIMENT

The apparatus of this invention can be employed in various modes of operation, as will be taught by the methods described hereinafter, to provide a non-destructive testing tool applicable to structures of various geometries. For the purposes of illustration, the apparatus will be described in an application to on-line monitoring of pipe welding processes, providing a video display of the emissionn source location spectrum. The emission source location spectrum is a histogram of the emission data having an abscissa proportional to the pipers circumferential weld joint and an ordinate indicative of the number of emissions generated from a given location. Weld monitoring is performed during both the welding process and the subsequent cooling period. The logic circuitry, illustrated in FIG. 1, has six selectable operating modes for accommodating various geometries; however, the circuitry connected as shown is arranged for this particular illustrative application with the remaining modes of operation to be described hereinafter.

Figure 2:
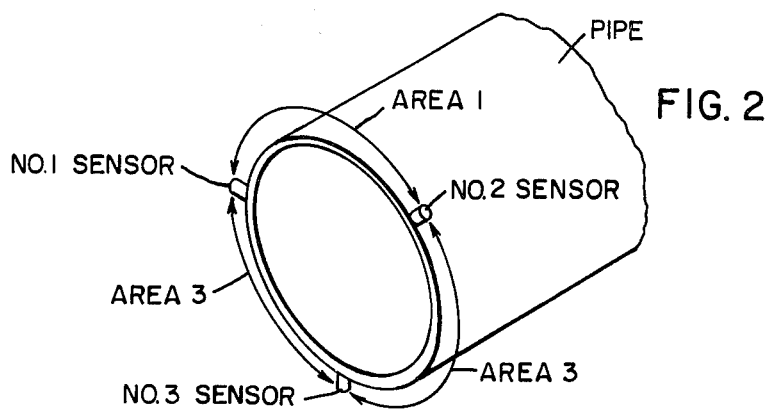
FIG. 2 is a isometric view of an exemplary workpiece under test illustrating the sensor locations employed by one operating mode of this invention.

In an application to monitoring a pipe circumferential weld joint three sensors are desirably mounted with 120° separation on the pipe girth in a location adjacent to the weld joint as illustrated in FIG. 2. The circuitry identifies the first two sensors detecting a given acoustic emission event and measures the difference in the time of reception at the two sensor locations. All subsequent events will be ignored until the source location is identified. Clock pulses, that are counted as a measure of the time difference, are set at a repetition rate equal to one tenth inch sound travel in the pipe wall. Thus, the time difference measurements are automatically translated into a distance measurement.

Figure 1:
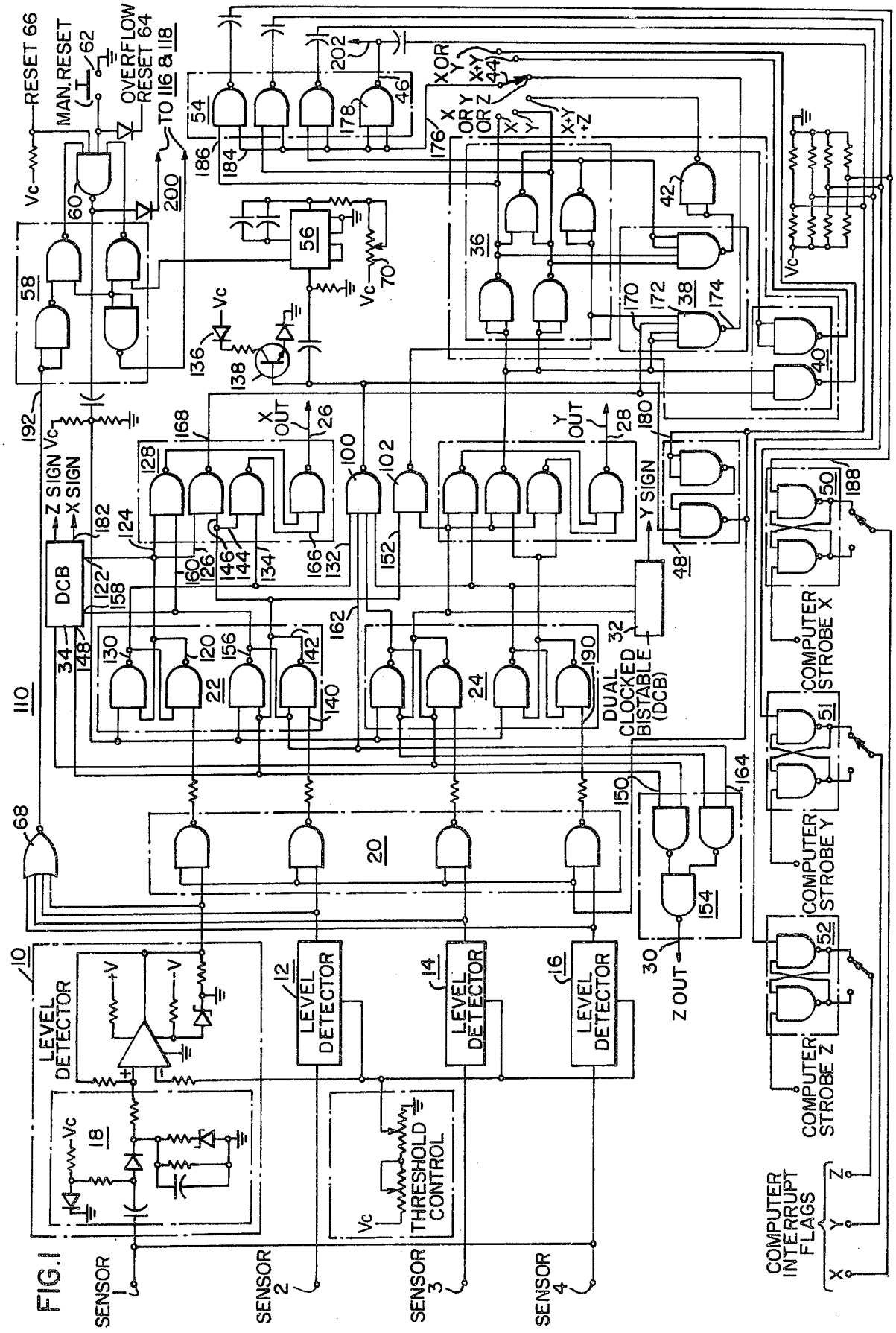
FIG. 1 is a schematic diagram of the basic electrical processing circuitry employed by this invention.
Figure 3:
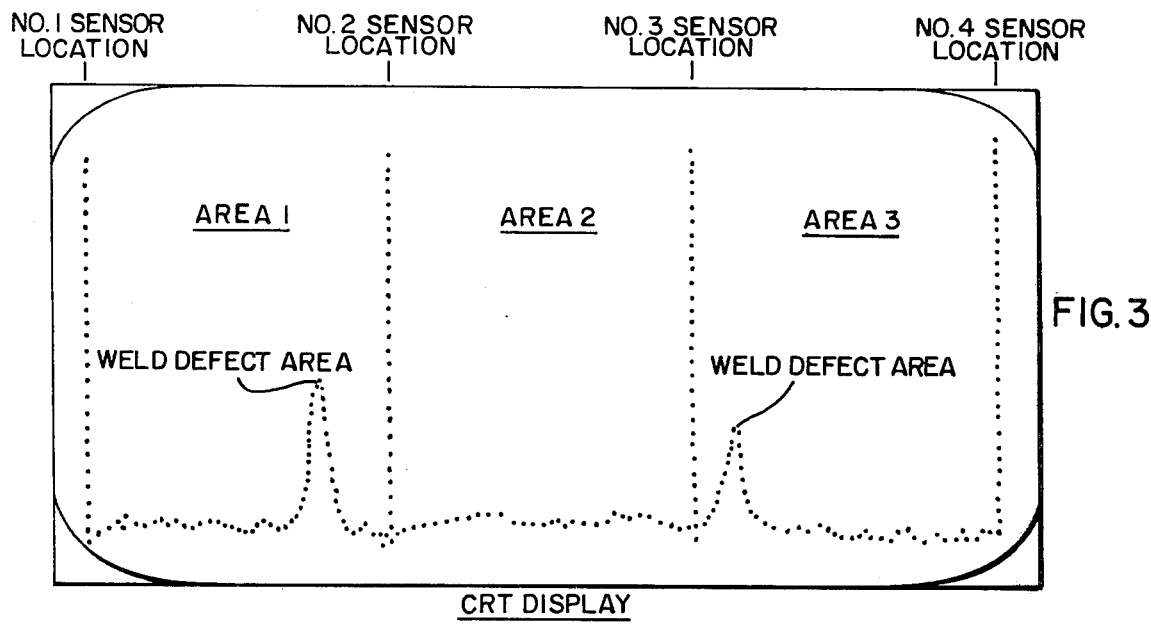
FIG. 3 is a graphic illustration of a representative readout identifying the source location of acoustic emissions.
Figure 4:
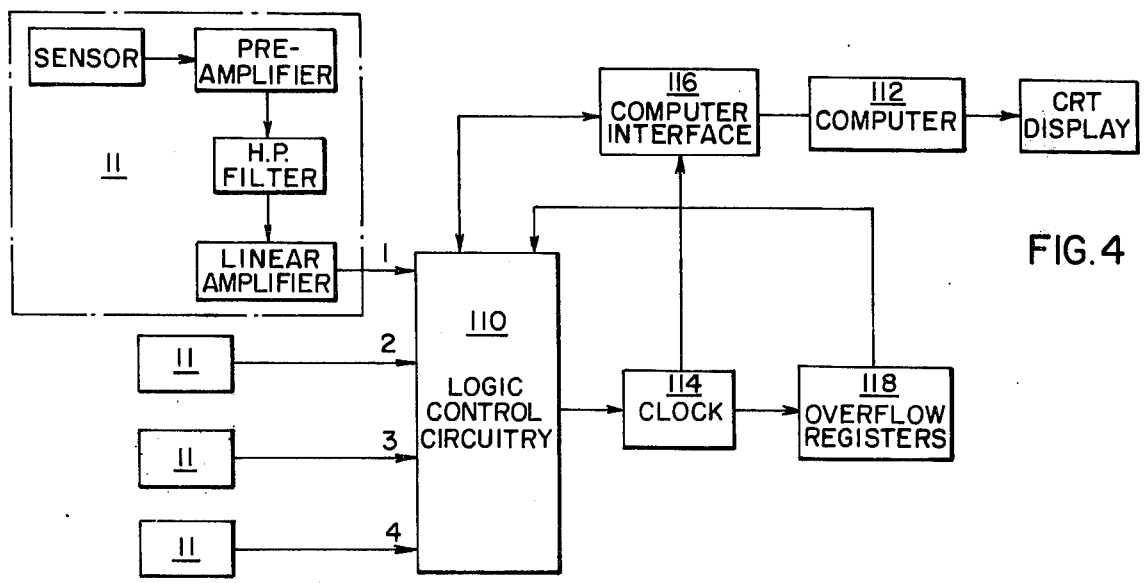
FIG. 4 is a block diagram of the monitoring system of this invention.

The circuitry 110 illustrated in FIG. 1 is designed to accomunicate a compatible set of output signals to a general purpose mini-computer 112, which can be any one of a number of computers readily available in the art, such as the PDP-8E mini-computer manufactured by the Digital Equipment Corporation, Maynard, Mass. The computer will perform some common analytical computations on the information supplied, to process the inputed signals to a form which identifies the source location of the emission in video format. The computer 112 is illustrated in block form in FIG. 4, which provides an overview of the interaction of the various components of the monitoring system of this invention. An exemplary source location spectrum is illustrated in FIG. 3 which shows weld defects identified in areas 1 and 3. The pipe diameter is supplied to the computer by way of a teletype keyboard to calibrate the abscissa of the video display. The ordinate ranges are selected by adjusting sense switches on the computer console.

Referring to FIG. 1 it will be appreciated that the circuitry shown is generally adaptable to accommodate four monitoring sensors, however, in this particular application only three are employed. The signals obtained from the sensors are respectively communicated to corresponding channels 1, 2 and 3 with the fourth channel interconnected to channel 1 so that channels 1 and 4 are common to sensor 1. Circuit modules 10, 12, 14 and 16 are identical level detectors, which stabilize the DC level of the sensor outputs and block spurious noise signals. The capacitor-resistor-diode filter networks 18 at the input to each level detector are utilized for noise rejection. The outputs of the respective level detectors are communicated to corresponding NAND gates which form a four-channel gate network 20 that functions to inhibit the processing of sensor responses communicated subsequent to the reception of a given acoustic event by two of the three sensor locations until data processing is complete. Thus, signals detected on the remaining input channel are ignored by the computer. Bistable latch circuits 22 and 24 will latch in response to appropriate detected signals communicated by the gate network 20 until signal processing is complete and the latch reset to accept new data.

A signal detected between input channels 1 and 2 will be represented by an X output at terminal 26 having a duration equal to the difference in time between reception at the corresponding sensor locations. Similarly, a signal detected between input channels 3 and 4 will be represented by a Y output at terminal 28 and a signal detected between channels 2 and 3 will be represented by a Z output at terminal 30. The X, Y and Z outputs are communicated to the clock 114 to gate clock pulses to the computer interface 116 and overflow resistors 118 shown in FIG. 4. Inasmuch as channels 1 and 4 are connected in common for tubular monitoring applications, signals present on channels 3 and 4 will be processed as if communicated by channels 3 and 1. Circuit modules 32 and 34 are responsive to the first sensor detecting a signal to provide corresponding reference signs for the X, Y and Z outputs. Gate combinations 36, 38, 40 and 42 function to determine when a selected data set condition has been satisfied as prescribed by the selected operating mode.

As previously explained the circuit illustrated in FIG. 1 has a programmable capability that will accommodate five distinct and six separate modes of operation. The six position switch 44 programs the internal circuitry to accommodate each mode. In the position shown in FIG. 1 the circuitry is selected to function in a pipe monitoring application identified in the figure as the X OR Y OR Z operating mode. This particular mode of operation prescribes a number of selected data set conditions that control the circuit to accept the first two sensor responses, blocking all subsequent sensor outputs. The difference in reception time of the two sensors monitored is clocked by an oscillator, generally illustrated in FIG. 4 by reference character 114, having repetition rate corresponding to a one-tenth inch spacial separation on the pipe girth. The first sensor reception is identified by a corresponding output sign. Thus, switch 44 couples the appropriate operating mode and arranges the circuits 36, 38, 40 and 42 to determine when a selected data set condition has been satisfied. When a data set condition has been satisfied, the differentiated output signal 46 of gate 178 is communicated to a bistable latch 48, which in turn closes the input gates 20 until reset by an appropriate command signal. The outputs from gates 54 are similarly differentiated and are employed to set computer flags 50, 51 and 52, which are recognized by the computer and reset by the computer data strobes once the incoming data has been processed. The computer interrupt flags are communicated to and interpreted by the computer to identify the particular data to be inputed. An adjustable monostable 56 provides a time delay, as selected by the operator, that must be satisfied before the processing circuitry can be reset. Preferably, the reset delay time is adjusted to either equal the signal travel time between the closest pair of sensors or to allow the acoustic signal to decay within the monitored material. The delay will thus function to prevent multiple data entries for the same event. A manual reset 62, overflow reset 64 or a reset 66 from the computer will be latched by circuit arrangements 58 and 60 until all reset parameters are met, i.e. NOR gate 68 does not indicate that any input signals are present and the present time delay has expired.

The clock signal, gated by the appropriate X, Y, or Z output is inputed into corresponding computer interface registers 116, which store the information until accepted by the computer in response to a computer interrupt flag, and to limit-selectable overflow registers 118. A high limit on the overflow registers is preferably set to initiate a reset command to terminal 64 when a single channel detects an event which is not subsequently detected on an adjacent channel within the time required for an emission signal to travel the distance equal to the closest sensor separation. The reset command initiates a reset signal at terminal 200 to all the registers and the logic circuitry and readies the system to accept additional data once the hold-time delay engendered by monostable 56 has expired.

For the purpose of illustrating the operation of the circuit just described programmed in the X or Y or Z monitoring mode, assume an acoustic event is first monitored by sensor 1, and next by sensor 2, and then by sensor 3, appropriate signals will then first appear across the input terminals to channels 1 and 4.

The signal detected by the sensor associated with channel 1 activates threshold control circuit 10, passes through the appropriate gate 20 and sets the corresponding bistable latch 22. A positive logic level results on output terminal 120 of latch network 22, which is propagated to input 122 of the dual gated bistable 34 and to inputs 124 and 126 of the quad NAND gate network 128. Additionally, a negative logic level is set on output 130 of logic network 22, which is propagated to input terminal 132 of NAND gate 100 and input terminal 134 of the quad NAND gate arrangement 128. The related logic levels enable the negative level on input 134 to set the X output appearing at terminal 26 negative. The negative X output enables the clock pulses to accumulate in the X register of the computer interface 116 and to accumulate in the corresponding overflow register 118 as can generally be appreciated by reference to FIG. 4. The negative level on input 132 of gate 100 sets a positive level on the output of gate 100 which biases the base of transistor 138 rendering the emitter to collector junction conductive, and, in turn, activating the light emitting diode 136 as an indication to the operator that the circuit is processing data. The positive level appearing at the output of gate 100 is simultaneously differentiated to trigger the hold time monostable 56. Through the positive level appearing at the output of gate 100 is also propagated to the bistable latch 48, the latch will only set in response to a negative level signal and therefore remains in its present state.

In this illustrative example, the sensor associated with channel 2 was next assumed to monitor the acoustic event. The corresponding signal communicated through threshold control circuit 12 is progated to the input 140 of the bistable latch network 22. The resulting negative output at terminal 142 is communicated to input terminals 144 and 146 of gate network 128, input terminal 148 of the dual clock bistable 34, input 150 of gate network 154, and input 152 of gate 102. Additionally, a negative level is set on output 156 of latch network 22 which is in turn communicated to input 158 of monostable 34, input 160 of NAND gate network 128, input 162 of NAND gate 100 and input 164 of NAND gate arrangement 154. The positive level appearing on input 144 of NAND arrangement 128 changes the output 166 back to a negative level, which changes the X output appearing at terminal 26 to a positive level and gates off the clock output 114 to the X computer interface register and X overflow register. Simultaneously, the positive level appearing on input 146 of gate network 128 is combined with the positive level on input 126 of the same gate to produce a negative output 168 which is propagated to the input 170 of NAND gate 172. The terminals of NAND gate 172 are so arranged to provide an "or" logical function so that a negative level input 170 provides a positive output at terminal 174. Inasmuch as the data set conditions for the X or Y or Z operating mode have been satisfied, a positive "store enable" level is propagated to the input 176 of NAND gate 178. The output of gate 178 will in turn provide a negative "clock hold" level 202 to gate off the clock pulse to the overflow and interface registers. Additionally, the negative going level on output 46 of gate 178 is differentiated and communicated to inputs 180 of bistable latch 48 and the latch is set to disable all input gates 20, which in turn prevent additional acoustic events from altering the current data logic. The output of dual clocked bistable 34, appearing at terminal 182, is set to reflect that sensor 1 monitored the acoustic event prior to sensor 2 and propagates the proper sign to the X computer interface register. The positive "store enable" level is also monitored on input terminal 184 of NAND gate arrangement 54, which is coincident with the positive X data level on input 186 of the same gate producing a negative output level. The output thus produced is differentiated and communicated to the input 188 of NAND arrangement 50 to set the X computer interrupt flag. The X interrupt flag output signals the computer to strobe the X data into the core memory.

In the particular operating mode under consideration the acoustic event monitored on channel 1 is also coupled to channel 4 and communicated through threshold control circuit 16 to input 190 of bistable latch 24. The input terminal 190 would normally set logic levels for a Y output condition, however, inasmuch as the input gates 20 are closed before a complete data set is monitored, i.e. no signal is received on sensor input channel 3 before a complete data set is received on the X output, the Y computer interrupt flag will not set and the computer will ignore the erroneous data in the Y interface register. Similarly, any data in the Z register will be ignored.

After the computer has inputed the valid data, it generates a "reset" signal that is monitored on terminal 66 of gate 60. A positive level is generated on the output of gate 60 and latched by gate arrangement 58 until the hole time generated by the monostable 56 has expired and no signal appears on the input 192 indicating that no signals are being communicated to the input channels as monitored by NOR gate 68. When these conditions are satisfied, i.e. the monostable hold time expired and no signal present on the input channels, the latch reset level is released and the output of gate 60 transistions negative. This negative change is differentiated and utilized to reset all four input latches within the gate arrangements 22 and 24. A reset level is also utilized to reset the computer interface registers and the overflow registers. When all input gates are reset, all input levels to NAND gate 100 assume the positive level and the output returns negative, ready to detect a new acoustic event monitored on any of the input sensors. In addition, when the output of gate 100 transitions negative, latch 48 is reset and all input gates, 20, are enabled.

Similarly, for all monitoring applications when the condition prescribed by the program select switch 44 is satisfied, the input gates 20, are disabled, the clock is disabled to the overflow and computer interface registers, the appropriate computer interrupt flags are set, and the computer transfers the valid data into the core memory. The computer then generates a reset signal which is held in a latched condition until the selected hold time has expired and no input signals are present as indicated by NOR gate 68. The latch reset is then released and the monitoring system is ready to accept additional data. Gated dual bistables 32 and 34 are utilized to detect the sequence in which an acoustic event is monitored and sends a plus or minus sign to the appropriate computer interface register for this purpose.

While the circuitry has thus far been described in an application to monitoring tubular geometries, five additional monitoring functions can be programmed by the selectable switch 44. Switch 44 arranges the logic circuitry 36, 38 and 42 to identify when the signals required to satisfy a particular data set condition governed by the mode of operation chosen has occurred. The X, Y and Z outputs are then compared to determine whether a particular data set condition has been satisfied. Once a given set of data conditions have been achieved, the appropriate computer interrupt flags are set.

As will be appreciated from the circuit connections, the X mode will process signals communicated to channels 1 and 2 by the corresponding sensors. Essentially, this mode of operation will indicate the position along a line between the two sensors, most proximate the source of the acoustic event monitored.

Mode Y will function in a similar manner to that of mode X, processing signals communicated to channels 3 and 4.

The X + Y mode employs all four channels to identify a point in a plane most proximate the source of an emission. The circuitry is arranged by the programmed connection implemented by the switch 44 in the X + Y position to monitor the time difference in reception respectively between channels 1 and 2, and 3 and 4. As before, if a given acoustic event is not monitored by a given number of sensors within a specified time period a reset signal will be provided to re-initiate the measurement. In this case all four sensors must respond within a time period governed by the front panel input 70.

The X + Y + Z programmed position employs all four monitoring channels and measures the time difference between signals received on channels 1 and 2, 2 and 3, and 3 and 4, supplying three separate sets of data.

The last programmed connection, designated X OR Y, employs all four sensors and measures the time difference in reception between the first pair of sensors showing a response, i.e. 1 and 2 or 3 and 4. The remaining sensor pair is inhibited from communicating an output to the processing circuitry.

Thus, this invention has the capability of detecting crack growth on a microscale and can locate the source location of a wide range of signal strengths generated within workpieces of varying geometries. Of particular benefit is the fact that the system can be employed in an on-line monitoring application for welding processes. Sensors are readily available that can withstand operating temperatures of 350° F, which is more than adequate for most welding processes. In addition, special high temperature sensors have been developed that will operate at 1000° F or higher. Further, inasmuch as all acoustic signals do not follow the same propagation in metal structures, and most welding processes generate acoustic noise signals, the satistical data processing techniques employed by the methods and apparatus of this invention have unique advantages in such an application.

I claim as my invention:

1. A method of monitoring the presence and source location of acoustic emissions generated within or on a tubular, acoustically conductive medium comprising the steps of:
   monitoring acoustic emissions respectively at a plurality of at least three separate spaced locations around the girth of the tubular surface;
   measuring the time difference between the first reception at one of the monitoring locations of a particular acoustic emission and the next reception of the same emission at a second of the monitoring locations;
   automatically blocking for a given period of time all further acoustic reception responses from the monitoring locations subsequent to the reception at the second monitoring location;
   translating the time measurement into a position measurement around the tubular girth representative of the girth location most proximate the source of the emission; and
   registering the position measurement.

2. The method of claim 1 wherein the blocking time is adjusted to at least the time required to register the position measurement.

3. The method of claim 2 wherein the measuring step is automatically re-initiated when the blocking time has passed.

4. The method of claim 1 wherein the translating step includes the step of identifying the two monitoring locations first receiving the acoustic emission.

5. The method of claim 4 including the step of identifying the monitoring location first receiving the acoustic emission.

6. The method of claim 1 wherein the measuring step is automatically re-initiated if the time difference exceeds a preset time interval.

7. The method of claim 6 wherein the preset time interval is selected to be less than the time required for the acoustic emission to travel a distance equal to the surface spatial separation between the monitoring location first receiving the emission and the next most proximate monitoring location.

8. The method of claim 1 wherein the time difference is measured in time increments respectively equal to the time required for the acoustic emission to traverse a one-tenth inch spatial separation on the tubular surface.

9. The method of claim 8 wherein the time difference is clocked by an oscillator having a cycle duration corresponding to one time increment.

10. The method of claim 1 wherein the monitoring locations are substantially equally spaced around the girth of the tubular surface.

11. Apparatus for monitoring the presence and source location of acoustic emissions generated within or on an acoustically conductive medium comprising:
   a plurality of acoustic sensors communicably coupled to the surface of the medium and respectively positioned at a corresponding plurality of spaced locations;

means for respectively measuring the difference in time between the reception of a given acoustic event at a pre-established combination of sensors;

means for blocking further acoustic reception responses from the monitoring locations subsequent to the reception by a predetermined number of the pre-established sensor combinations;

means for programming the measuring means and blocking means to re-establish the sensor combinational groupings and corresponding predetermined number of responses required before blocking in accordance with a plurality of given acoustical monitoring functions; and means for translating the time measurement into a position measurement on the surface representative of the location of the source of the emission; and means for registering the location of the emission source.

12. The apparatus of claim 11 including means for resetting the measuring means in the event an acoustic event is not received by a set number of sensors governed by the acoustic monitoring function programmed, within a given time interval.

13. The apparatus of claim 11 wherein said program means adjusts said measuring means to clock the difference in time between the first reception of a given acoustic emission at a sensor location and the next reception of the same emission at a sensor location and adjusts said blocking means to block subsequent acoustic responses.

14. The apparatus of claim 11 wherein the blocking means functions to block further receptions for a selected time interval.

15. The apparatus of claim 14 wherein the blocking time is adjusted to at least the time required to register the source location.

16. The apparatus of claim 14 wherein the measuring means is reset for a new measurement when the blocking time has passed.

17. The apparatus of claim 11 wherein said program means adjusts said measuring means to clock the difference in acoustic reception time respectively between the sensors in two separate sensor pairs and adjusts said blocking means to block subsequent acoustic response after reception at the four sensor locations which are a part of the paired groupings.

18. The apparatus of claim 11 wherein said program means adjusts said measuring means to clock the difference in acoustic reception time respectively between first and second, second and third, and third and fourth sensor locations and adjusts said blocking means to block subsequent acoustic responses after reception at the four sensor locations.

19. The apparatus of claim 11 wherein said program means adjusts said measuring means to monitor acoustic receptions by the sensors of two separate sensor pairs and clock the difference in acoustic reception time between the sensors in the first pair having an acoustic response, and adjusts the blocking means to block subsequent acoustic response after reception by both sensors of the pair being clocked.

* * * * *